(12) United States Patent
Kazanzides et al.

(10) Patent No.: US 11,244,508 B2
(45) Date of Patent: Feb. 8, 2022

(54) AUGMENTED REALITY DISPLAY FOR SURGICAL PROCEDURES

(71) Applicant: The Johns Hopkins University, Baltimore, MD (US)

(72) Inventors: Peter Kazanzides, Lutherville, MD (US); Long Qian, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/733,460

(22) PCT Filed: Jan. 25, 2019

(86) PCT No.: PCT/US2019/015112
§ 371 (c)(1),
(2) Date: Jul. 31, 2020

(87) PCT Pub. No.: WO2019/152269
PCT Pub. Date: Aug. 8, 2019

(65) Prior Publication Data
US 2020/0388075 A1  Dec. 10, 2020

Related U.S. Application Data

(60) Provisional application No. 62/625,979, filed on Feb. 3, 2018.

(51) Int. Cl.
*G06T 19/00* (2011.01)
*A61B 34/30* (2016.01)
(Continued)

(52) U.S. Cl.
CPC ............ *G06T 19/006* (2013.01); *A61B 34/30* (2016.02); *A61B 90/37* (2016.02);
(Continued)

(58) Field of Classification Search
None
See application file for complete search history.

(56) References Cited

U.S. PATENT DOCUMENTS

| 9,547,940 B1 | 1/2017 | Sun et al. |
| 2013/0111399 A1* | 5/2013 | Rose ..................... G06T 3/0025 715/800 |

(Continued)

FOREIGN PATENT DOCUMENTS

WO  2016207628 A1  12/2016

OTHER PUBLICATIONS

Azimi et al., (2012). Augmented reality goggles with an integrated tracking system for navigation in neurosurgery. In Proc. IEEE Virtual Reality, pp. 123-124, Orange County, CA.

(Continued)

*Primary Examiner* — Tapas Mazumder
(74) *Attorney, Agent, or Firm* — Harrity & Harrity, LLP

(57) ABSTRACT

A device may determine a view of a user of a head mounted display. The device may obtain tracking data relating to a surgical procedure. The device may obtain, from an imaging device, surgical imaging relating to the surgical procedure. The device may orient models of objects based on the tracking data and the view of the user of the head mounted display, wherein the objects includes the imaging device. The device may augment, by providing output to the head mounted display for display, the view of the user with contextual information relating to the objects based on orienting the models based on the tracking data and the view of the user, wherein the contextual information includes the surgical imaging captured by an imaging device.

20 Claims, 14 Drawing Sheets

(51) Int. Cl.
*A61B 90/00* (2016.01)
*G16H 40/67* (2018.01)
*G16H 40/20* (2018.01)
*G02B 27/01* (2006.01)
*A61B 34/20* (2016.01)
*A61B 90/50* (2016.01)

(52) U.S. Cl.
CPC ......... *G02B 27/0172* (2013.01); *G16H 40/20* (2018.01); *G16H 40/67* (2018.01); *A61B 2034/2072* (2016.02); *A61B 2090/365* (2016.02); *A61B 2090/502* (2016.02); *G02B 2027/0141* (2013.01); *G06T 2210/41* (2013.01)

(56) References Cited

U.S. PATENT DOCUMENTS

2017/0056115 A1* 3/2017 Corndorf ................ G16Z 99/00
2017/0312032 A1 11/2017 Amanatullah et al.
2018/0197624 A1* 7/2018 Robaina .............. G06F 16/2379

OTHER PUBLICATIONS

Azuma et al., (1994). Improving static and dynamic registration in an optical see-through HMD. In Proceedingsof the21st Annual Conference on Computer Graphics and Interactive Techniques, pp. 197-204. ACM.
Azuma., (1997). A survey of augmented reality. Presence: Teleoperators and Virtual Environments, 6(4):355-385.
Cobb et al., (1999). Virtual reality-induced symptoms and effects (VRISE). Presence, 8(2):169-186.
Dimaio et al., (2008). The da Vinci research interface. In MICCAI Workshop on Systems and Arch. for Computer Assisted Interventions, Midas Journal: http://hdl.handle.net/10380/1464.
Enquobahrie et al., (2012). Robot assisted prostate surgery using augmented reality with deformable models. In MICCAI Workshop on Systems and Arch. for Computer Assisted Interventions, Midas Journal: http://hdl.handle.net/10380/3362.
Guthart et al., (2000). The IntuitiveTM telesurgery system: Overview and application. In IEEE Intl. Conf. on Robotics and Automation (ICRA), pp. 618-621.
Janin et al., (1993). Calibration of head-mounted displays for augmented reality applications. In Virtual Reality Annual International Symposium, pp. 246-255. IEEE.
Kato et al., (1999). Marker tracking and HMD calibration for a video-based augmented reality conferencing system. In IEEE/ACM Intl. Workshop on Augmented Reality (IWAR), pp. 85-94.

Kazanzides et al., (2014). An open-source research kit for the da Vinci R © surgical robot. In IEEE Intl. Conf. on Robotics and Automation (ICRA).
Kazanzides, P., DiMaio, S., Deguet, A., Vagvolgyi, B., Balicki, M., Schneider, C., Kumar, R., Jog, A., Itkowitz, B., Hasser, C., and Taylor, R. (2010). The Surgical Assistant Workstation (SAW) in minimally-invasivesurgery and microsurgery. In MICCAI Workshop on Systems and Arch. for Computer Assisted Interventions, Midas Journal.
Lorensen et al., (1993). Enhancing reality in the operating room. In IEEE Conf. on Visualization, pp. 410-415. IEEE.
Martin-Gonzalez et al., (2009). Head-mounted virtual loupewith sight-based activation for surgical applications. In EEEIntl.Symp. on Mixed and Augmented Reality (ISMAR), pp. 207-208. IEEE.
Vagvolgyi et al., (2008). The Surgical Assistant Workstation: a software framework for telesurgical robotics research. In MICCAI Workshop on Systems and Arch. for Computer Assisted Interventions, Midas Journal: http://hdl.handle.net/10380/1466.
Navab et al., (1999).Merging visibleand invisible: Two camera-augmented mobile C-arm (CAMC) applications. In Proc. IEEE/ACM Intl. Workshop on Augmented Reality (IWAR), pp. 134-141. IEEE.
Navab et al., (2012). First deployments of augmented reality in operating rooms. Computer, 7(45):48-55.
Qian et al., (2016a). Modeling physical structure as additional constraints for stereoscopic optical see-through headmounted display calibration. In IEEE Intl. Symp. on Mixed and Augmented Reality (ISMAR). IEEE.
Qian et al., (2016b). Reduction of interaction space in Single Point Active Alignment Method for optical see-through head-mounted display calibration. In IEEE Intl. Symp. on Mixed and Augmented Reality (ISMAR). IEEE.
Sadda et al., (2013). Surgical navigation with a head-mounted tracking system and display. In MedicineMeets Virtual Reality (MMVR) 20, pp. 363-369.
Sgarbura et al., (2010). The decisive role of the patient-side surgeon in robotic surgery. Surgical Endoscopy, 24 (12):3149-3155.
Tuceryan et al., (2000). Single point active alignment method (SPAAM) for optical see-through HMD calibration for AR. In Proc. IEEE/ACM Intl. Symp. on Augmented Reality (ISAR), pp. 149-158.
Qian et al., "ARssist: Augmented Reality on a Head-Mounted Display for the First Assistant in Robotic Surgery", IET Research Journals, 2018, 6 pages.
Qian et al., "Augmented Reality Assisted Instrument Insertion and Tool Manipulation for the First Assistant in Robotic Surgery", 2018, 7 pages.
International Search Report and Written Opinion for Application No. PCT/US2019/015112, dated May 16, 2019, 8 pages.

* cited by examiner

AUGMENTED REALITY DISPLAY FOR SURGICAL PROCEDURES

CROSS-REFERENCE TO RELATED APPLICATIONS

This application is a 371 national stage of PCT Application PCT/US2019/015112 filed on Jan. 25, 2019, entitled "AUGMENTED REALITY DISPLAY FOR SURGICAL PROCEDURES," which claims priority to U.S. Provisional Patent Application No. 62/625,979, filed on Feb. 3, 2018, both of which are hereby expressly incorporated by reference herein.

BACKGROUND

In many surgical procedures, such as minimally invasive surgery, a surgical team does not have direct visualization of surgical instruments and the patient anatomy and often rely on images obtained from cameras inserted into the patient's body. These images are generally not aligned with the surgeon's viewpoint of the patient, which can lead to hand-eye coordination challenges.

Minimally-invasive robotic surgery may involve teamwork between a surgeon and a patient-side assistant. Performance of the patient-side assistant affects quality of the robotic surgery and patient outcomes. The patient-side assistant may perform trocar placement, docking and undocking of a surgical robotics device, insertion of laparoscopic instruments, hemostatic maneuvers, and/or the like. However, in a robot-enabled operating room with a surgical robotics device, a display for laparoscope video may be positioned at a vision cart. Further, preoperative images may be displayed on another display on a separate console or as a window within a surgeon console outside of the robot-enabled operating room. As a result, the patient-side assistant may frequently switch positions to perform different tasks and view multiple displays to view information relating to the different tasks. Further, the patient-side assistant may compensate for differing orientations between imaging provided for display and an actual position of the patient-side assistant when performing imaging-guided procedures.

SUMMARY

According to some implementations, a system may include an imaging device to capture surgical imaging relating to a surgical procedure, a tracking device to capture tracking information relating to the surgical procedure, a display to provide augmented imaging relating to the surgical procedure, and a visualization platform. The visualization platform may receive input data relating to the surgical procedure, wherein the input data includes the surgical imaging, received from the imaging device, and wherein the input data includes the tracking information, received from the tracking device. The visualization platform may generate the augmented imaging based on the input data, wherein generating the augmented imaging comprises: determining an orientation for the augmented imaging based at least in part on an orientation of the display, a pose of one or more objects tracked in the tracking information, and an orientation of the surgical imaging, and augmenting the input imaging to include oriented contextual information relating to the objects tracked in the tracking information and to include the surgical imaging. The visualization platform may provide, to the display, the augmented imaging.

According to some implementations, a device may include one or more memories, and one or more processors, communicatively coupled to the one or more memories, to receive surgical imaging of a surgical procedure, wherein the surgical imaging includes imaging captured by a surgical imaging device. The one or more processors may receive location tracking information associated with identifying a location of a plurality of objects, wherein the plurality of objects include the surgical imaging device and a surgical implement. The one or more processors may determine the location of the plurality of objects based on the location tracking information. The one or more processors may correlate the location of the plurality of objects to determine a relative position of the plurality of objects and a display. The one or more processors may generate augmented imaging based on the relative position of the plurality of objects and the display. The one or more processors may provide the augmented imaging for display via the display.

According to some implementations, a method may include determining, by a device, a view of a user of a head mounted display. The method may include obtaining, by the device, tracking data relating to a surgical procedure. The method may include obtaining, by the device and from an imaging device, surgical imaging relating to the surgical procedure. The method may include orienting, by the device, objects based on the tracking data and the view of the user of the head mounted display, wherein the objects includes the imaging device. The method may include augmenting, by the device and by providing output to the head mounted display for display, the view of the user with contextual information relating to the objects based on orienting the objects based on the tracking data and the view of the user, wherein the contextual information includes the surgical imaging captured by an imaging device.

DETAILED DESCRIPTION

Figure 1:
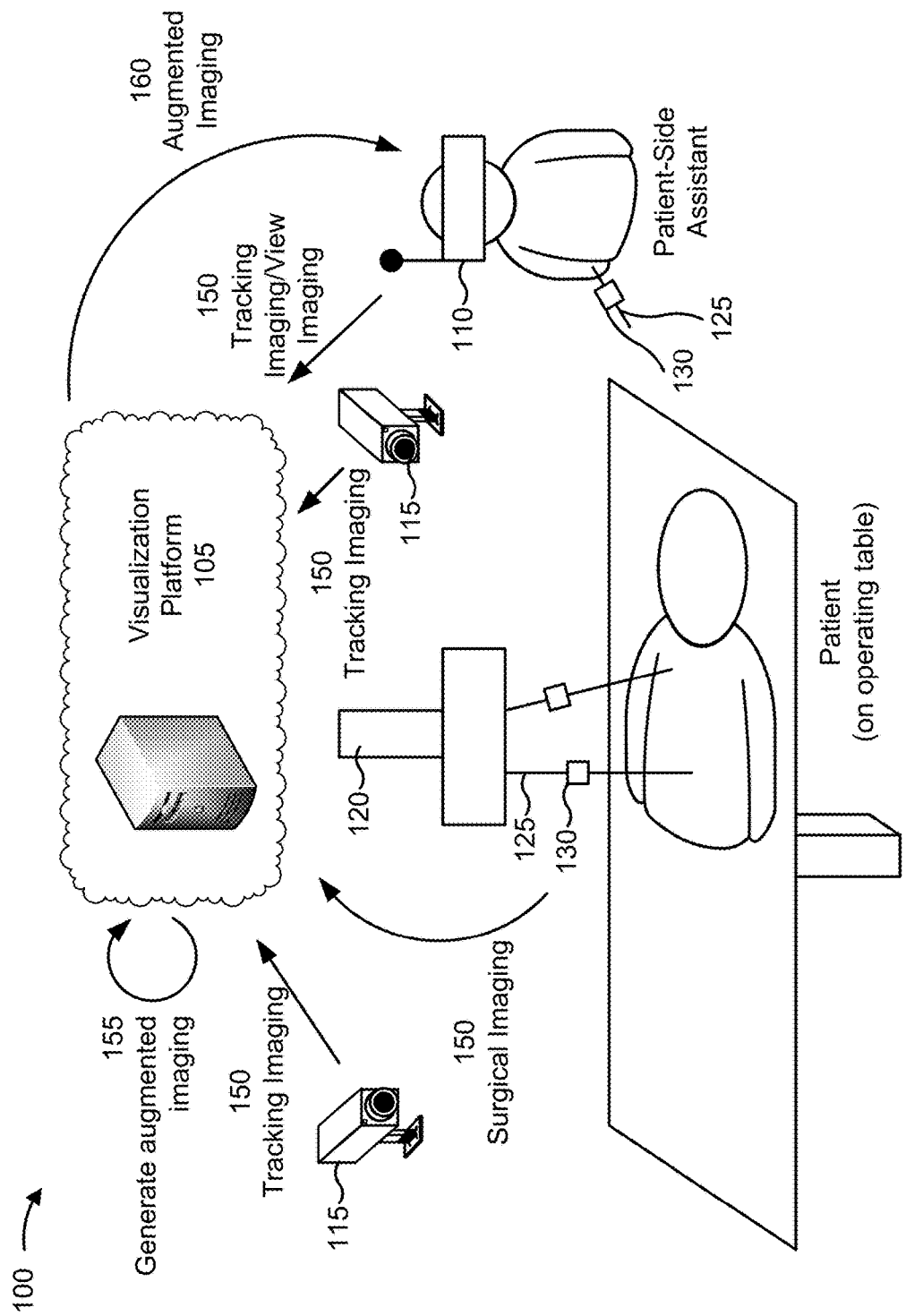
FIG. 1 is a diagram of an example implementation described herein.

The following detailed description of example implementations refers to the accompanying drawings. The same reference numbers in different drawings may identify the same or similar elements.

As described above, a patient-side assistant may move between multiple different positions to perform surgical tasks and to view imaging relating to the surgical tasks. Such movement may increase a difficulty of surgical procedures, and may result in an increased likelihood of errors or negative patient outcomes.

Some implementations described herein relate to a surgical system with an integrated head-mountable display and surgical robotics device. The head-mountable display may be an optical, see-through head mounted display. The head-mountable display may be configured to display visualizations of hand-held and robotic instruments inside the patient, endoscopic video, and/or preoperative medical images of the patient using augmented imaging. Although some implementations are described in terms of a head-mountable display, other types of displays are possible, such as another type of wearable display, a handheld display, and/or the like.

A visualization platform may generate visualizations, composites of visualizations, and/or the like. In this way, the visualization platform may reduce a need of the patient-side assistant to switch positions to perform different surgical tasks and view imaging relating to the different surgical tasks. The visualization platform may provide augmented reality in connection with a head-mountable display by compositing multiple views and by virtually displaying occluded surgical instruments and endoscope probes (e.g., occluded by surgical draping, by a patient's body, and/or the like). By combining an augmented reality platform with a surgical robotics device, improved clinical benefits may be achieved by improving situation awareness and ergonomics for the patient-side assistant.

Some implementations described herein may use an optical see-through head-mountable display (OST-HMD) or a video see-through head-mountable display (VST-HMD). An OST-HMD may be used to combine the user's view of a patient and virtual graphics objects. This may reduce a likelihood of failure (if the OST-HMD fails, a patient-side assistant will still see through optics thereof). Moreover, an OST-HMD may reduce a likelihood of motion-sickness relative to a VST-HMD. Some implementations described herein may provide tracking and registration of surgical implements. For example, the visualization platform may cause an OST-HMD to overlay occluded portions of surgical implements and/or video from an endoscope with a real view of a patient.

Further, the visualization platform may provide a view of surgical imaging, such as laparoscopic video, for display, while still enabling the patient-side assistant to see a real view of the patient. In this way, by providing a composition of multiple views using augmented imaging techniques, the visualization platform reduces a need for patient-side assistants to switch focus and/or position for different tasks, thereby reducing fatigue and improving situational awareness, which may improve patient outcomes. For example, in a tool insertion task as described in more detail herein, a patient-side assistant may need to place a surgical implement under a field of view of an endoscope, and coordinate with a main surgeon controlling the surgical implement and/or the endoscope. During insertion, the visualization platform may generate augmented imaging to provide an indicator of a relative position of the surgical implement and an indicator of an orientation of the endoscope. In this way, difficulty in quickly and accurately moving the surgical implement to a desired position may be reduced. Some implementations described herein may perform coordinate transformations between the different devices and/or surgical implements to enable generation of augmented imaging.

FIG. 1 is a diagram of an example implementation 100 described herein. As shown in FIG. 1, example implementation 100 may include a visualization platform 105, a head-mountable display 110 used by a patient-side assistant, a set of devices 115 (which may include a set of tracking devices for locating positions of entities within an operating room, a set of imaging devices for obtaining medical imaging of a patient, and/or the like), and a surgical robotics device 120. In some implementations, surgical robotics device 120 may include one or more surgical implements 125. Similarly, the patient-side assistant may hold a surgical implement 125. In some implementations, a particular surgical implement 125 may include a fiducial marker 130 to enable motion tracking of the particular surgical implement 125.

As further shown in FIG. 1, and by reference number 150, the set of devices 115 (e.g., tracking devices, imaging devices, etc.) may provide input data to visualization platform 105 for processing. For example, a set of cameras mounted in an operating room may provide tracking information (e.g., tracking imaging or other types of tracking information) of the operating room to enable a determination of a pose (e.g., a position, an orientation, a location, etc.) of a surgical implement 125. In some implementations, the input data may be three-dimensional imaging (e.g., from a depth imaging camera). In some implementations, a tracking device may not be a camera. For example, an electromagnetic tracking system may provide input data that determines the location of a surgical implement 125.

In some implementations, visualization platform 105 may receive surgical imaging (e.g., endoscopic imaging) from an endoscope attached to a surgical implement 125. In some implementations, the endoscope may be a monoscopic endoscope or a stereoscopic endoscope. In some implementations, head-mountable display 110 may include a device 115 to enable view imaging of a view of a patient-side assistant to be captured using head-mountable display 110 and provided to visualization platform 105. In some implementations, visualization platform 105 may receive non-real time surgical imaging. For example, visualization platform 105 may receive pre-operative surgical imaging (e.g., from a surgical device, such as a magnetic resonance imaging (MRI) device, from a server, such as a hospital patient record server, and/or the like).

In some implementations, visualization platform 105 may obtain other information relating to a surgical procedure. For example, visualization platform 105 may communicate with surgical robotics device 120 to determine a type of surgical implement 125 that is being operated by surgical robotics device 120, a pose of a surgical implement 125, and/or the like. Additionally, or alternatively, surgical robotics device 120 may receive information identifying a pose of devices 115, a pose of the patient-side assistant (e.g., a location and/or orientation of head-mountable display 110), and/or the like. In some implementations, visualization platform 105 may receive patient data, such as data from a patient record, data from a medical device monitoring the patient (e.g., a heart rate monitor, a blood pressure monitor, etc.), and/or the like.

As further shown in FIG. 1, and by reference number 155, visualization platform 105 may process the input imaging to generate augmented imaging. For example, visualization platform 105 may determine a pose (e.g., a location, an orientation, a position, etc.) for the augmented imaging. In this case, visualization platform 105 may determine a pose of the patient-side assistant (e.g., an orientation of head-mountable display 110), and may generate augmented imaging that matches the pose of the patient side assistant. In other words, visualization platform 105 may determine an orientation of an endoscope type of surgical implement 125 relative to an orientation of head-mountable display 110, and may transform surgical imaging captured by the endoscope to align the input imaging captured by the endoscope to the orientation of the patient-side assistant using head-mountable display 110. For example, visualization platform 105 may cause the surgical imaging to appear at a particular location in a display, angled at a particular angle in the display, and/or the like. In some implementations, visualization platform 105 may generate the augmented imaging based on input from a user. For example, head-mountable display 110 may capture a gesture command, a voice command, and/or the like, and may trigger display of augmented imaging, an alteration to the augmented imaging, and/or the like.

Additionally, or alternatively, visualization platform 105 may determine a pose of a handheld surgical implement 125 being held by and/or positioned by the patient-side assistant. For example, when a portion of the handheld surgical implement 125 is occluded, visualization platform 105 may generate a projection of the handheld surgical implement 125 based on a model of the handheld surgical implement 125, and may cause the projection to be provided for display so that the patient-side assistant can view the handheld surgical implement 125 despite the handheld surgical implement 125 being occluded.

In some implementations, visualization platform 105 may transform surgical imaging based on determining the orientation for the augmented imaging. For example, visualization platform 105 may rotate imaging from an endoscope type of surgical implement 125 based on a position of the patient-side assistant, thereby causing transformed imaging from the endoscope to match a perspective of the patient-side assistant. In this way, a difficulty in maneuvering the surgical implement 125 being held by and/or positioned by the patient-side assistant may be reduced relative to imaging that is not re-oriented based on a position of the patient-side assistant.

In some implementations, visualization platform 105 may augment the transformed imaging with contextual information. For example, visualization platform 105 may overlay a view of the transformed imaging of the endoscope in a view of the patient-side assistant via the head-mountable display 110, such that the view of the endoscope is overlaid at a position of the endoscope, as described in more detail herein. Additionally, or alternatively, visualization platform 105 may overlay patient data in a view of the patient assistant to reduce a necessity of the patient-side assistant repositioning or reorienting to view a monitor showing patient data. Additionally, or alternatively, visualization platform 105 may show a field-of-view indicator identifying an orientation of an endoscope, a projection of an occluded portion of a surgical implement 125, and/or the like.

As further shown in FIG. 1, and by reference number 160, visualization platform 105 may provide the augmented imaging to head-mountable display 110. For example, visualization platform 105 may cause head-mountable display 110 to provide the augmented imaging for display based on generating the augmented imaging. In this case, visualization platform 105 may periodically or continuously update the augmented imaging based on changes to the input imaging, changes to poses of the patient-side assistant and/or the surgical implements 125, and/or the like. In some implementations, visualization platform 105 may use information regarding the input imaging to generate a three-dimensional anatomical model of a patient, and may provide augmented imaging based on the three-dimensional anatomical model (e.g., an estimated visualization from another angle that is not directly captured in input imaging).

As indicated above, FIG. 1 is provided merely as one or more examples. Other examples may differ from what is described with regard to FIG. 1.

Figure 2A:
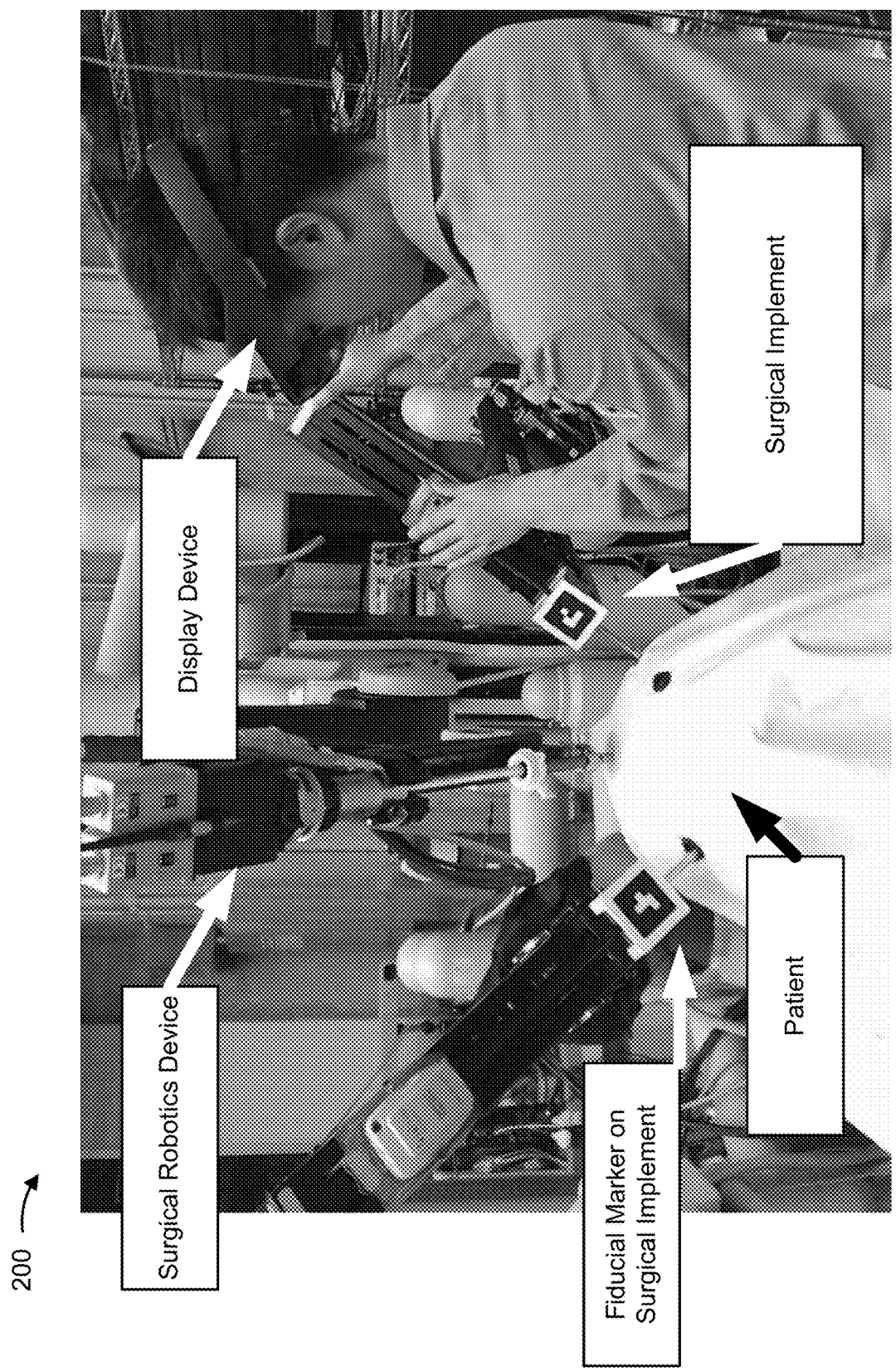
FIGS. 2A and 2B are diagrams of example implementations described herein.
Figure 2B:
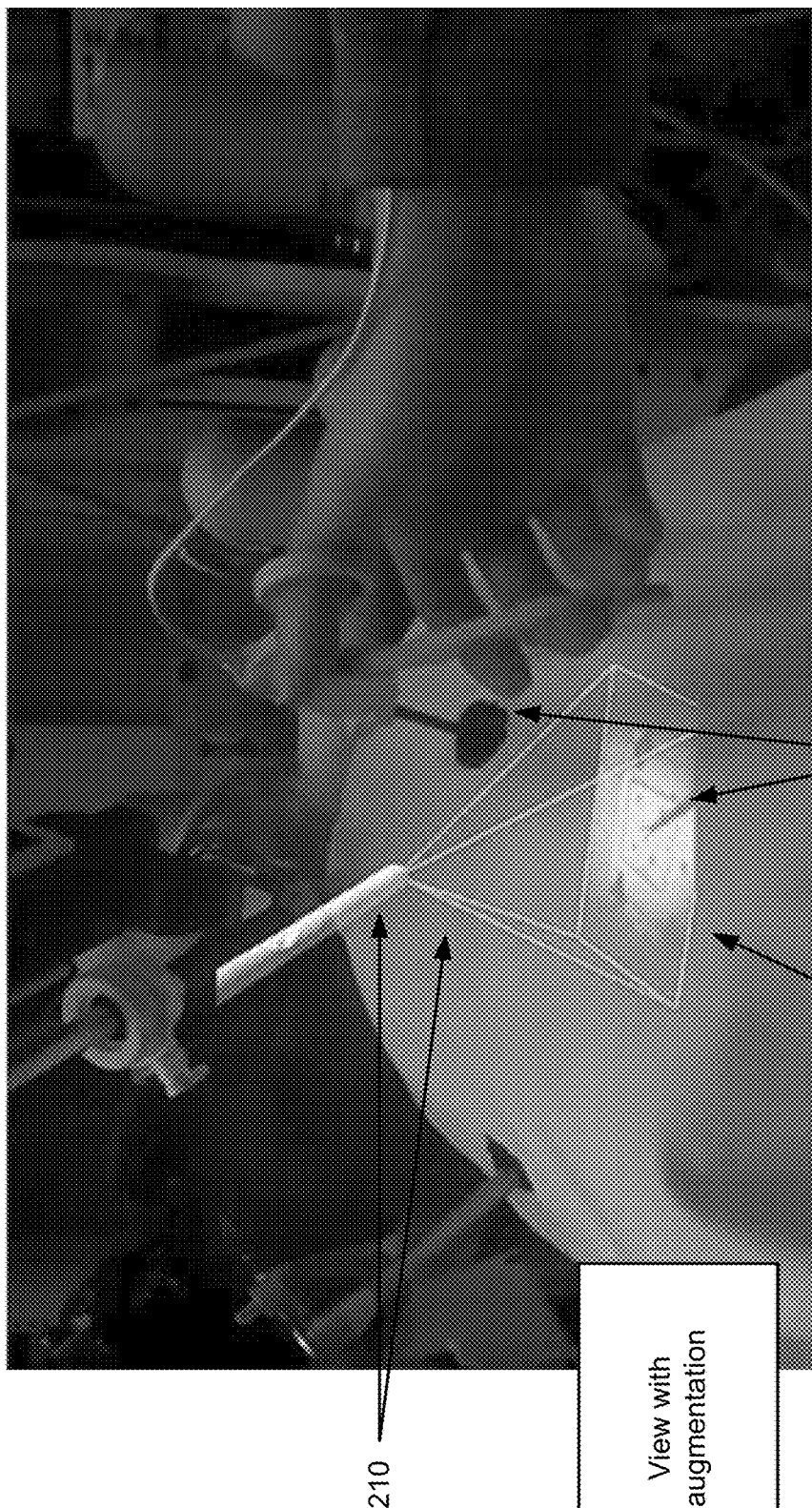

FIGS. 2A-2C are diagrams of an example implementation 200 described herein.

As shown in FIG. 2A, a patient-side assistant may wear a display device (e.g., a head-mountable display) while operating a surgical implement to assist in a surgical procedure performed on a patient. A surgical robotics device may operate another surgical implement (e.g., an endoscope) onto which a fiducial marker is attached. A visualization platform, as described herein, may be connected to the display device, the surgical robotics device, one or more imaging devices (not shown), and/or the like.

FIG. 2B shows a view of augmented imaging provided by the display device based on processing by the visualization platform. As shown by reference number 210, the visualization platform may augment the input imaging to show a field-of-view of an endoscope and a projection of the endoscope inside the patient (e.g., a projection of an occluded portion of the endoscope based on processing the input imaging to determine a location of the endoscope). In this way, the visualization platform may assist the patient-side assistant in orienting movement of a surgical implement to imaging provided by the endoscope.

As further shown in FIG. 2B, and by reference number 220, the visualization platform may overlay endoscopic imaging into a field-of-view of the patient-side assistant at a location that the imaging is being captured. For example, as shown by reference number 230, movements of the surgical implement by the patient-side assistant may be shown in the endoscopic imaging. In this case, the visualization platform may re-orient the endoscopic imaging to a common coordinate system. For example, the visualization platform may determine relative poses of the endoscope and the patient-side assistant, and may rotate the endoscopic imaging, tilt the endoscopic imaging, skew the endoscopic imaging, and/or the like.

In this way, the visualization platform may obviate a need of the patient-side assistant to compensate for or may reduce a difficulty in compensating for differing orientations of the patient-side assistant and the endoscope. In other words, when the patient-side assistant faces an opposite direction as the endoscope, without transformation, the patient-side assistant would need to reverse movements and compensate for an angled pose. In contrast, by transforming the endoscopic imaging, the endoscopic imaging may be flipped to the patient-side assistant's perspective or may have the angled pose corrected to enable more intuitive use of a surgical instrument. This may reduce a likelihood of errors in surgical procedures, and may improve patient outcomes.

As indicated above, FIGS. 2A and 2B are provided merely as one or more examples. Other examples may differ from what is described with regard to FIGS. 2A and 2B.

Figure 3A:
FIGS. 3A-3C are diagrams of example implementations described herein.
Figure 3B:
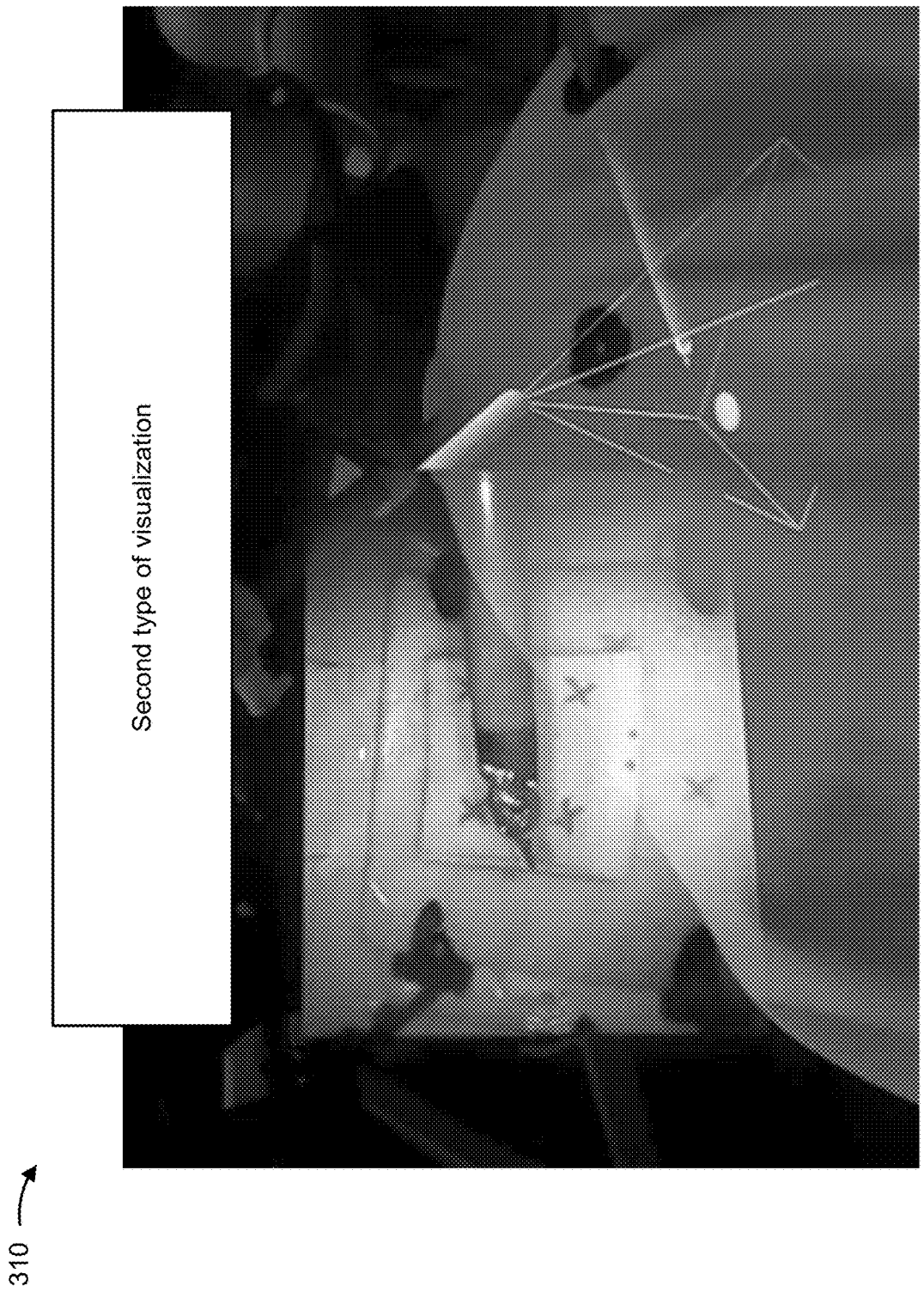
Figure 3C:
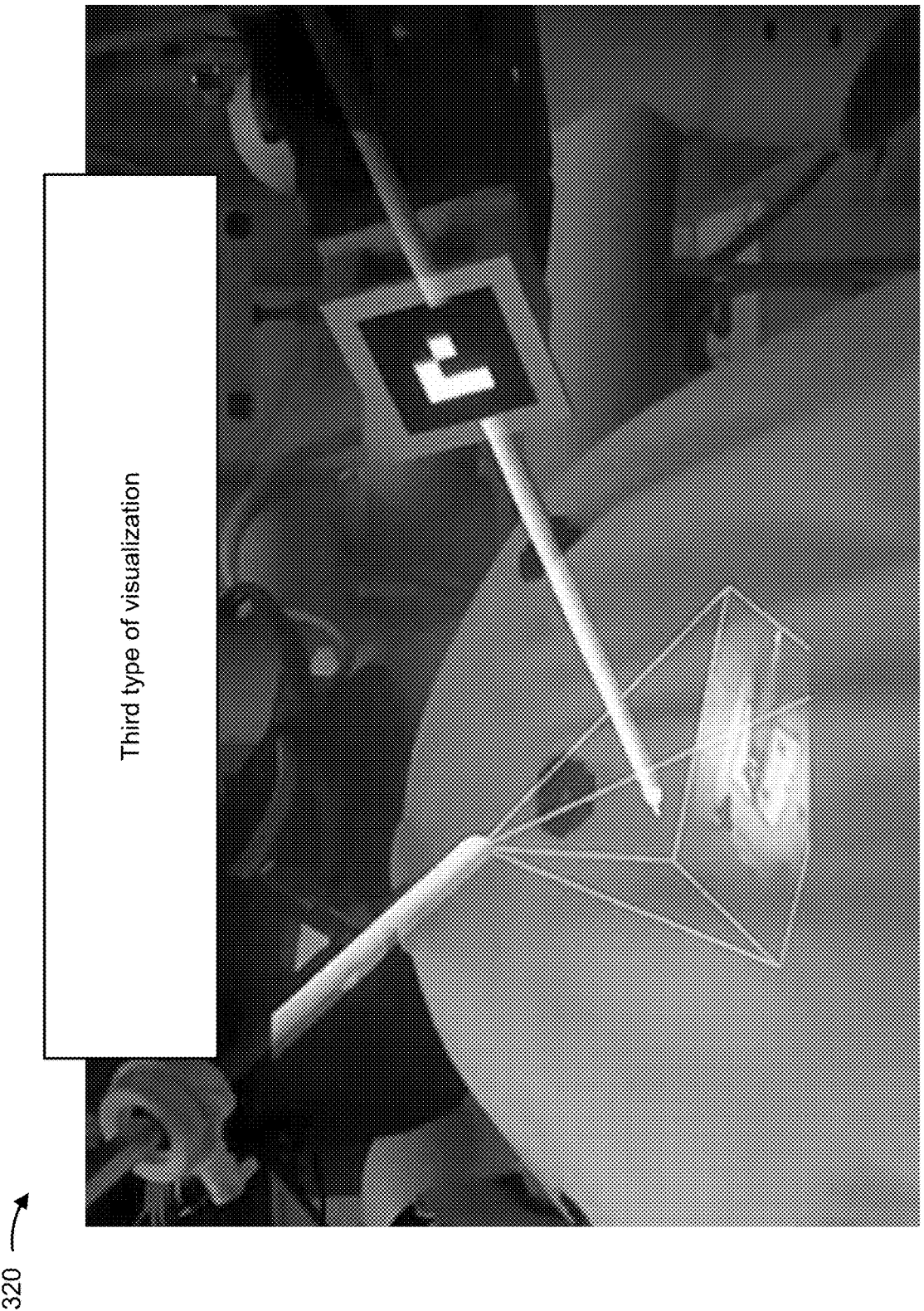

FIG. 3A-3C are diagrams of example implementations 300, 310, and 320 described herein. FIGS. 3A-3C show examples of types of visualizations (of endoscopic video and surgical robotics implements) provided by a visualization platform described herein for display via a head-mountable display.

As shown in FIG. 3A, example implementation 300 shows a first type of visualization, which may be termed a heads-up display type of visualization. In this case, the heads-up display type of visualization may include an overlay of endoscopic imaging at a fixed position in a view of a user of a head-mountable display (i.e., the visualization is fixed with respect to the head-mountable display).

As shown in FIG. 3B, example implementation 310 shows a second type of visualization, which may be termed a virtual monitor type of visualization. In this case, the virtual monitor type of visualization may include a virtual monitor in a field of view of the user, thereby obviating a need for a physical monitor to be deployed in an operating room.

As shown in FIG. 3C, example implementation 320 shows a third type of visualization, which may be termed an in-situ visualization. In this case, the in-situ visualization shows the endoscopic imaging overlaid in the frustum projection augmented into the view of the patient-side assistant. In this case, the endoscopic imaging may be rotated, skewed, tilted, and/or the like to match the frustum projection, as described above.

Any of the visualization modes shown in FIGS. 3A-3C may include augmented imaging showing a field-of-view indicator (e.g., a frustum projection) showing an orientation of endoscopic imaging provided in the virtual monitor. In this case, the visualization platform may generate a visualization of an endoscope field of view as a geometric object (e.g., based on characteristics of the endoscope, such as scope type, focal length, view angle, etc.).

In some implementations, characteristics of the endoscope may be determined based on measurement/calibration, based on manufacturer documentation, and/or the like. In some implementations, a depth of a geometric object may be set to a particular pre-configured value, based on expected distance to the anatomy, and/or the like. In some implementations, the orientation of the endoscope video (i.e., top left corner of the image shown on the monitor to the main surgeon) may be designated by a feature such as the circle shown in FIG. 3B.

As indicated above, FIGS. 3A-3C are provided merely as one or more examples. Other examples may differ from what is described with regard to FIGS. 3A-3C.

Figure 4:
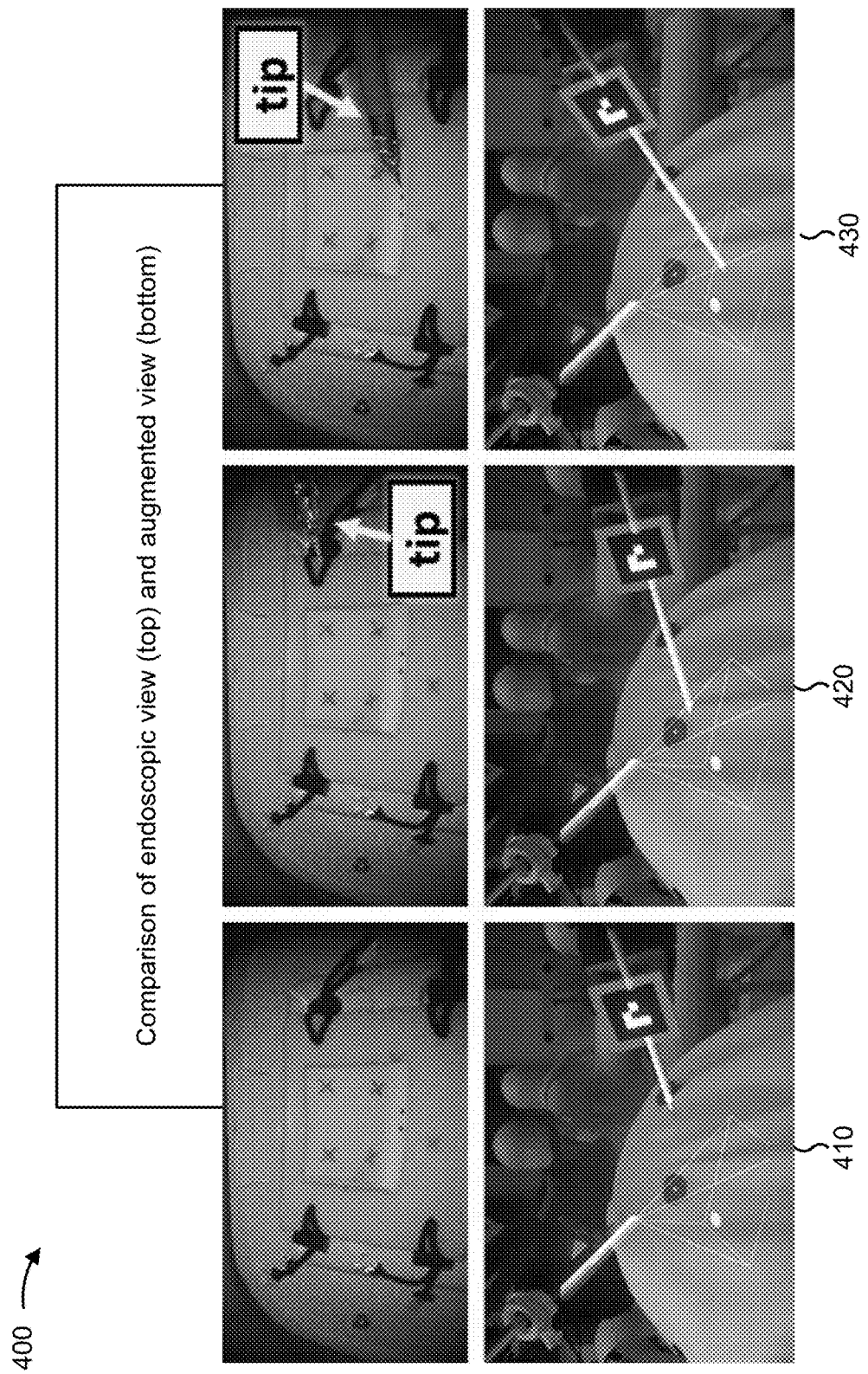
FIG. 4 is a diagram of an example implementation described herein.

FIG. 4 is a diagram of an example implementation 400 described herein. FIG. 4 shows an example of insertion of a surgical implement using augmented imaging described herein.

As shown in FIG. 4, and by reference number 410, before the surgical implement is in view of endoscopic imaging, the augmented view shows a field-of-view indicator of endoscopic imaging and the surgical implement before insertion. In some implementations, the endoscopic imaging may be provided via a heads-up display visualization, a virtual monitor visualization, an in-situ visualization, and/or the like. In some implementations, a visualization platform may obtain a three-dimensional model of the surgical implement (e.g., such as by communication with a surgical robotics device and/or a server associated therewith), and may augment the three-dimensional model of the implement into the augmented view. In some implementations, the visualization platform may generate a model of the surgical implement based on imaging of the surgical implement (e.g., captured by imaging devices within an operating room), and may augment the generated model of the surgical implement into the augmented view. For example, the visualization platform may capture imaging of a hand-held surgical implement, may generate a model of the hand-held surgical implement, and may augment a view of a user using the model of the hand-held surgical implement (e.g., such as to show the hand-held surgical implement when a portion of the hand-held surgical implement is obscured by an anatomy, by surgical draping, and/or the like.

As further shown in FIG. 4, and by reference number 420, when the surgical implement is inserted into view of the endoscopic imaging, a tip of the implement becomes visible in the endoscopic view. Based on the surgical implement being occluded by surgical draping, the augmented imaging includes a projection of the surgical implement.

As further shown in FIG. 4, and by reference number 430, the visualization platform may correlate a pose of the tip of the implement to a position in the field-of-view of the endoscope to enable the pose of the tip to be accurately rendered in a projection of the tip in the augmented view when the tip of the implement is occluded from view.

As indicated above, FIG. 4 is provided merely as one or more examples. Other examples may differ from what is described with regard to FIG. 4.

Figure 5:
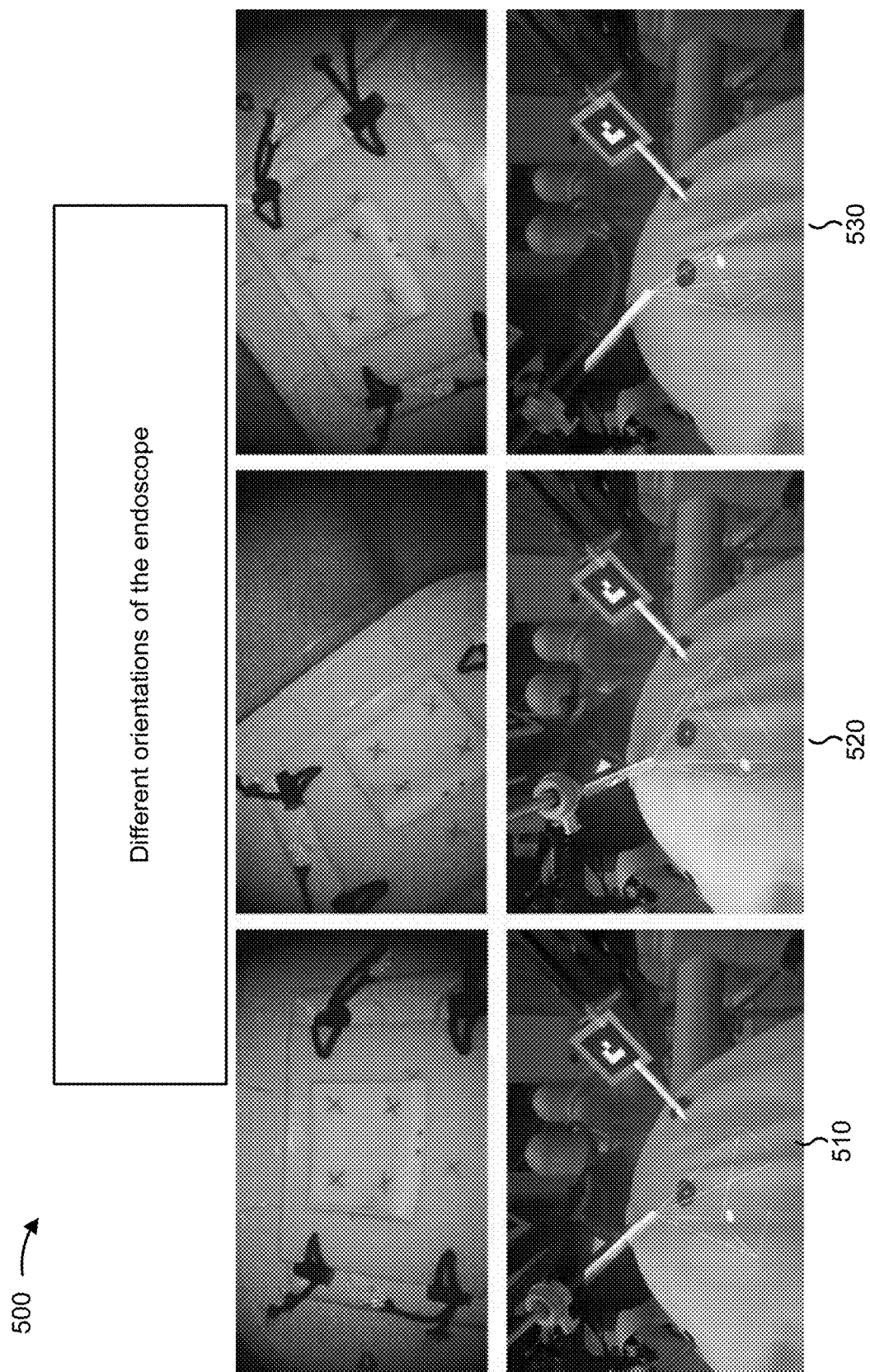
FIG. 5 is a diagram of an example implementation described herein.

FIG. 5 is a diagram of an example implementation 500 described herein. FIG. 5 shows endoscopic imaging and augmented imaging as an orientation of an endoscope is altered.

As shown in FIG. 5, and by reference number 510, a visualization platform provides, for display via a display device, a first field-of-view indicator in the augmented imaging based on a first orientation of the endoscope. As shown by reference number 520, when the orientation of the endoscope is altered, the first field-of-view indicator is altered to generate a second field-of-view indicator in the augmented imaging based on a second orientation of the endoscope. Similarly, as shown by reference number 530, when the orientation of the endoscope is altered again, the second field-of-view indicator is altered to generate a third field-of-view indicator showing a third orientation of the endoscope. In some implementations, endoscopic imaging may be skewed, tilted, rotated, and/or the like to match an orientation of the field-of-view indicator. Although some implementations are described herein in terms of altering the orientation of the endoscope, the orientation of the endoscope may be a relative orientation. Thus, an alteration to a position or orientation of a user of a head-mountable display may result in an alteration to an augmentation to accurately render an orientation of the endoscope relative to the user of the head-mountable display.

As indicated above, FIG. 5 is provided merely as one or more examples. Other examples may differ from what is described with regard to FIG. 5.

Figure 6:
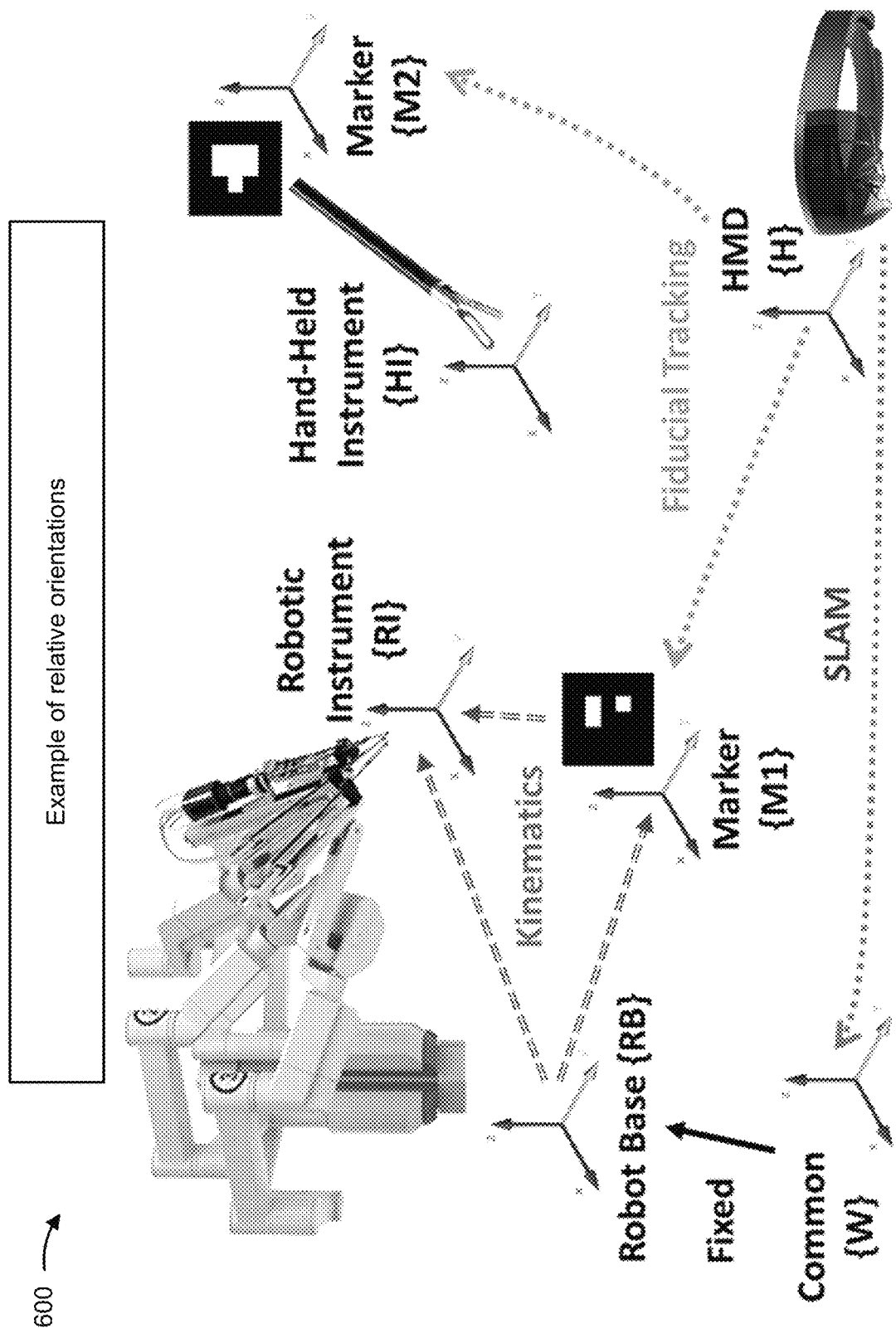
FIG. 6 is a diagram of an example implementation described herein.

FIG. 6 is a diagram of an example implementation 600 described herein. FIG. 6 illustrates a schematic diagram of relative poses of components of a system. The visualization platform may establish a common coordinate system (Common) for the components using a tracking procedure and a calibration procedure. The visualization platform may correlate coordinate systems of a robot base (e.g., of a surgical robotics device, which may be fixed), a robotic instrument (e.g., a surgical implement, which may be tracked based on a fiducial marker), a hand-held instrument (e.g., a surgical implement, which may be tracked based on a fiducial marker), and/or the like. In some implementations, the visualization platform may perform a tracking procedure and a calibration procedure to determine relative positions of each component, and align coordinate systems of each component to the common coordinate system to enable generation of augmented imaging.

In some implementations, the visualization platform may, when performing the tracking procedure, provide a real-time update of a transformation between different objects. In some implementations, the visualization platform may, when performing the calibration procedure (e.g., a subsequent calibration procedure after an initial calibration procedure), compensate for system error accumulated due to the bias during the tracking.

The visualization platform may use kinematics data of a surgical robotics device to determine a transformation between a surgical robotics device tool coordinate system and the surgical robotics device base coordinate system at runtime. In some implementations, fiducial markers, such as augmented reality (AR) tags, may be positioned on one or more arms of the surgical robotics device and/or on a base of the surgical robotics device. Using imaging of the fiducial markers from an imaging tracking device of a head-mountable display, the visualization platform may determine a transformation between a coordinate system of the head-mountable display (defined with respect to the imaging tracking device) and the surgical robotics device base coordinate system. In some implementations, the visualization platform may track multiple fiducial markers at the same time, thereby providing a further benefit of having redundant information. In this case, the visualization platform may implement sensor fusion methods to improve the overall system accuracy.

In some implementations, fiducial markers may be affixed to track surgical implements held by a patient-side assistant. In this case, one or more external optical tracking systems (e.g., imaging devices external to a head-mountable display) may provide imaging to the visualization platform to increase a likelihood of maintaining the fiducial markers in view relative to using only imaging from the head-mountable display-based imaging device.

In some implementations, with the integration of surgical robot kinematics and optical tracking via the head-mountable display-based imaging device and an external tracking system, the visualization platform may relate all the components within a common coordinate system. In this case, the visualization platform may relate the common coordinate system to eyes of a user of the head-mountable display. As an example, for OST-HMDs, the visualization platform may model the user's eye and the screen embedded in the glasses as a virtual camera, with the eye located at the focal point and the screen representing the imaging plane. In this case, in order for the augmented virtual objects to appear registered with corresponding real counterparts seen by the user, a user-specific display calibration may be performed by the visualization platform. In some implementations, the visualization platform may perform a single point active alignment method (SPAAM) based calibration technique.

In some implementations, the visualization platform may determine a spatial relationship between a head-mountable display and other objects within an operating room using a simultaneous localization and mapping (SLAM) based technique.

As indicated above, FIG. 6 is provided merely as one or more examples. Other examples may differ from what is described with regard to FIG. 6.

Figure 7:
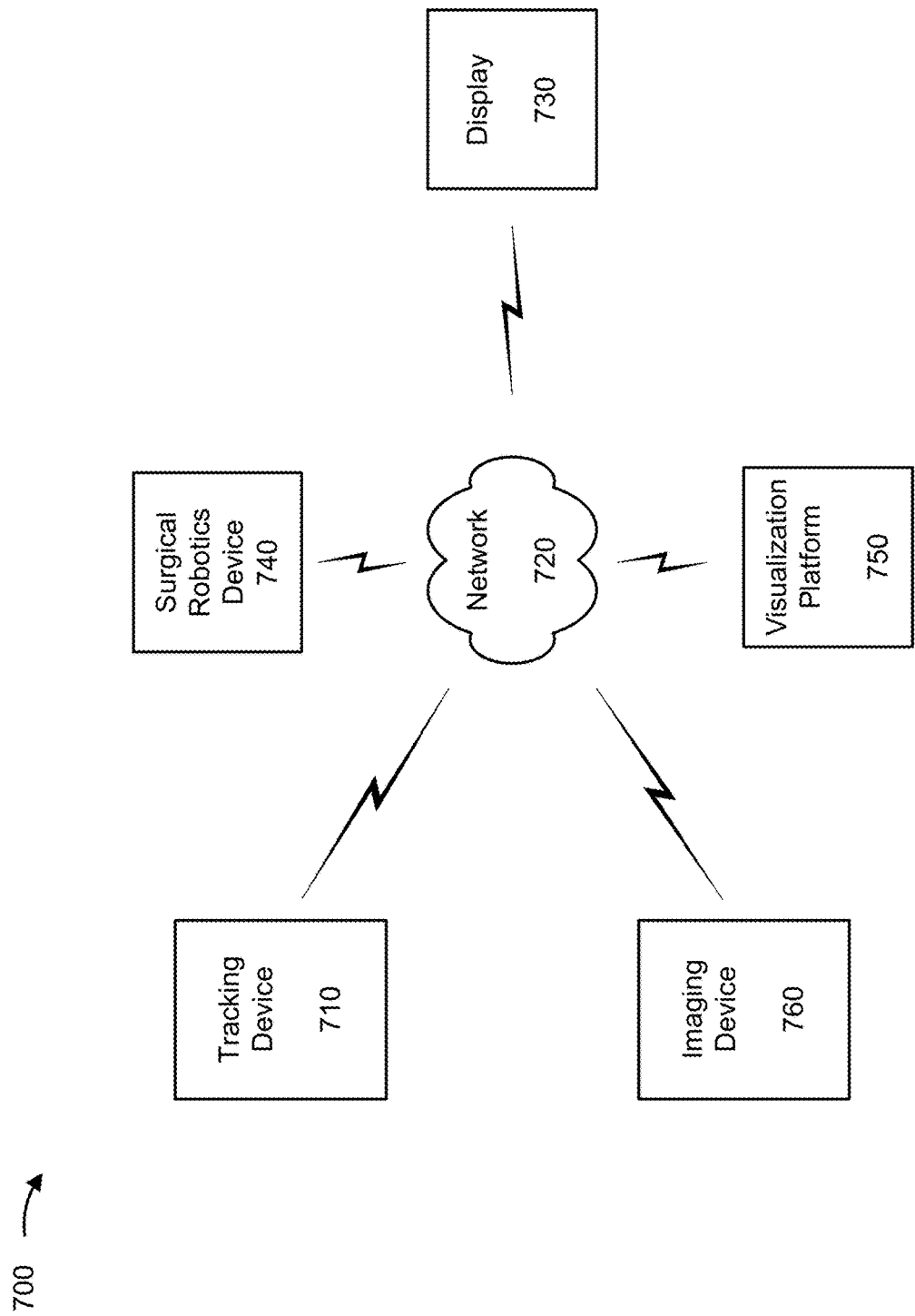
FIG. 7 is a diagram of an example environment in which systems and/or methods described herein may be implemented.

FIG. 7 is a diagram of an example environment 700 in which systems and/or methods described herein may be implemented. As shown in FIG. 7, environment 700 may include a tracking device 710, a network 720, a display 730, a surgical robotics device 740, a visualization platform 750, and an imaging device 760. Devices of environment 700 may interconnect via wired connections, wireless connections, or a combination of wired and wireless connections.

Tracking device 710 includes one or more devices capable of receiving, generating, processing, and/or providing tracking information. For example, tracking device 710 may include a camera, a video camera, a stereoscopic camera, a motion tracking device, and/or the like. Additionally, or alternatively, when tracking device 710 is a tracking device, tracking device 710 may include non-imaging devices, such as Bluetooth beacon-based tracking devices, electromagnetic tracking devices, triangulation-based tracking devices, trilateration-based tracking devices, etc.

Network 720 includes one or more wired and/or wireless networks. For example, network 720 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

Display 730 includes any display that is capable of presenting imaging provided by visualization platform 750. Display 730 may include technologies, such as liquid crystal displays (LCDs), light-emitting diode (LED) displays, plasma displays, wearable displays (e.g., head-mountable displays), handheld displays, and/or the like. Examples of display 730 may include an OST-HMD or a VST-HMD. Additionally, or alternatively, display 730 may be a non-wearable display, such as a handheld computer, a tablet computer, and/or the like. In some implementations, display 730 may be a stereoscopic or three-dimensional display.

Surgical robotics device 740 includes one or more devices capable of receiving, generating, storing, processing, and/or providing information associated with imaging and/or a surgical procedure. For example, surgical robotics device 740 may include a surgical robot with a set of surgical implements to perform image capture (e.g., an endoscope), surgical incision, and/or the like.

Visualization platform 750 includes one or more devices capable of receiving, generating, storing, processing, and/or providing information associated with generating augmented imaging. For example, visualization platform 750 may include an image processing system of display 730, an external image processing server connected to display 730, a cloud computing environment-implemented image processing platform, and/or the like. In some implementations, visualization platform 750 may provide output to display 730 for display.

Imaging device 760 includes one or more devices capable of capable of receiving, generating, processing, and/or providing medical imaging information. For example, imaging device 760 may include a camera, a video camera, a stereoscopic camera, a robot-mounted camera, and/or the like.

The number and arrangement of devices and networks shown in FIG. 7 are provided as one or more examples. In practice, there may be additional devices and/or networks, fewer devices and/or networks, different devices and/or networks, or differently arranged devices and/or networks than those shown in FIG. 7. Furthermore, two or more devices shown in FIG. 7 may be implemented within a single device, or a single device shown in FIG. 7 may be implemented as multiple, distributed devices. Additionally, or alternatively, a set of devices (e.g., one or more devices) of environment 700 may perform one or more functions described as being performed by another set of devices of environment 700.

Figure 8:
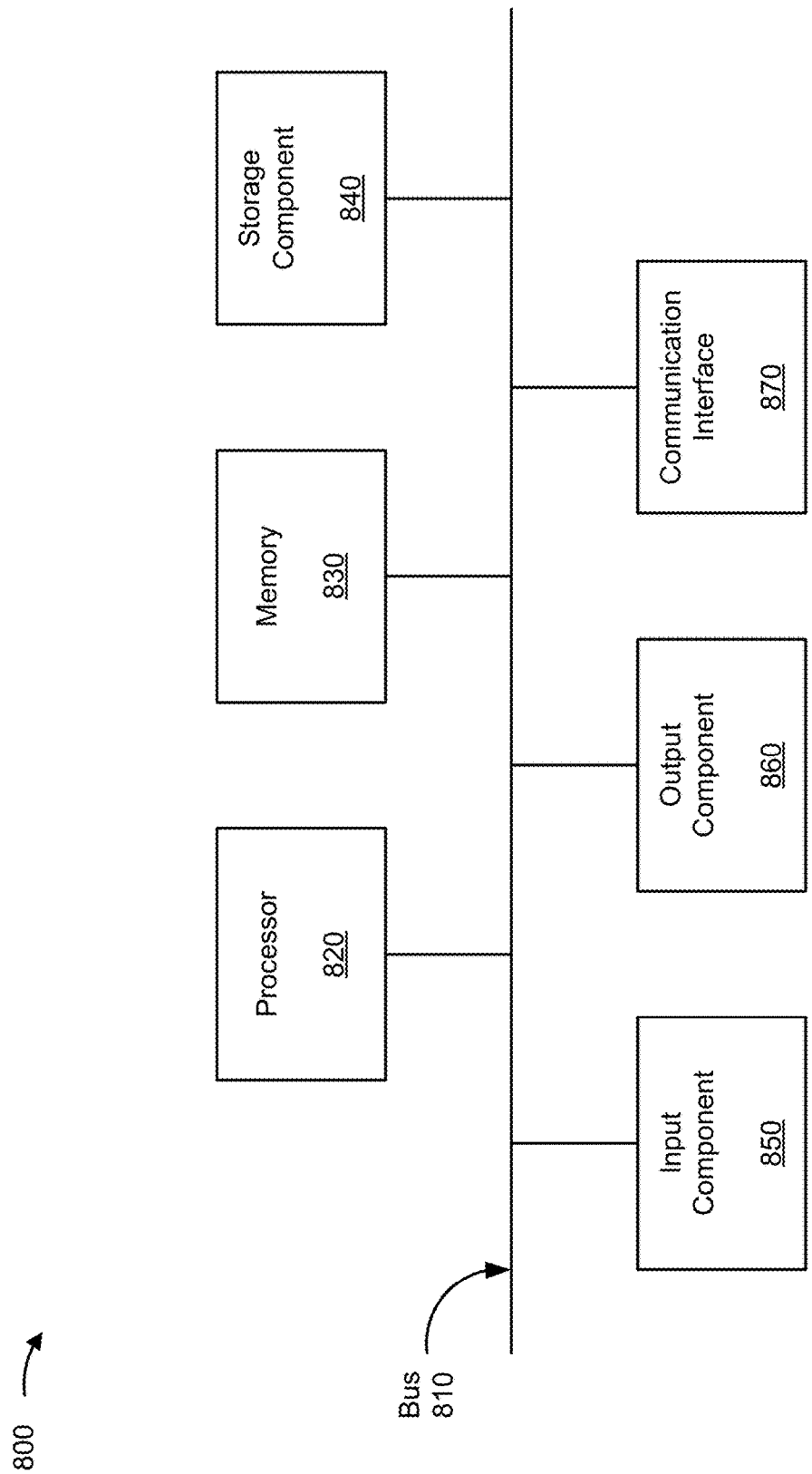
FIG. 8 is a diagram of example components of one or more devices of FIG. 7.

FIG. 8 is a diagram of example components of a device 800. Device 800 may correspond to tracking device 710, display 730, surgical robotics device 740, visualization platform 750, and/or an imaging device 760. In some implementations, tracking device 710, display 730, surgical robotics device 740, visualization platform 750, and/or imaging device 760 may include one or more devices 800 and/or one or more components of device 800. As shown in FIG. 8, device 800 may include a bus 810, a processor 820, a memory 830, a storage component 840, an input component 850, an output component 860, and a communication interface 870.

Bus 810 includes a component that permits communication among multiple components of device 800. Processor 820 is implemented in hardware, firmware, and/or a combination of hardware and software. Processor 820 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 820 includes one or more processors capable of being programmed to perform a function. Memory 830 includes a random access memory (RAM), a read only memory (ROM), and/or another type of dynamic or static storage device (e.g., a flash memory, a magnetic memory, and/or an optical memory) that stores information and/or instructions for use by processor 820.

Storage component 840 stores information and/or software related to the operation and use of device 800. For example, storage component 840 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 850 includes a component that permits device 800 to receive information, such as via user input (e.g., a touch screen display, a keyboard, a keypad, a mouse, a button, a switch, and/or a microphone). Additionally, or alternatively, input component 850 may include a component for determining location (e.g., a global positioning system (GPS) component) and/or a sensor (e.g., an accelerometer, a gyroscope, an actuator, another type of positional or environmental sensor, and/or the like). Output component 860 includes a component that provides output information from device 800 (via, e.g., a display, a speaker, a haptic feedback component, an audio or visual indicator, and/or the like).

Communication interface 870 includes a transceiver-like component (e.g., a transceiver, a separate receiver, a separate transmitter, and/or the like) that enables device 800 to communicate with other devices, such as via a wired connection, a wireless connection, or a combination of wired and wireless connections. Communication interface 870 may permit device 800 to receive information from another device and/or provide information to another device. For example, communication interface 870 may include an Ethernet interface, an optical interface, a coaxial interface, an infrared interface, a radio frequency (RF) interface, a universal serial bus (USB) interface, a Wi-Fi interface, a cellular network interface, and/or the like.

Device 800 may perform one or more processes described herein. Device 800 may perform these processes based on processor 820 executing software instructions stored by a non-transitory computer-readable medium, such as memory 830 and/or storage component 840. As used herein, the term "computer-readable medium" refers to a non-transitory memory device. A memory device includes memory space within a single physical storage device or memory space spread across multiple physical storage devices.

Software instructions may be read into memory 830 and/or storage component 840 from another computer-readable medium or from another device via communication interface 870. When executed, software instructions stored in memory 830 and/or storage component 840 may cause processor 820 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 8 are provided as an example. In practice, device 800 may include additional components, fewer components, different components, or differently arranged components than those shown in FIG. 8. Additionally, or alternatively, a set of components (e.g., one or more components) of device 800 may perform one or more functions described as being performed by another set of components of device 800.

Figure 9:
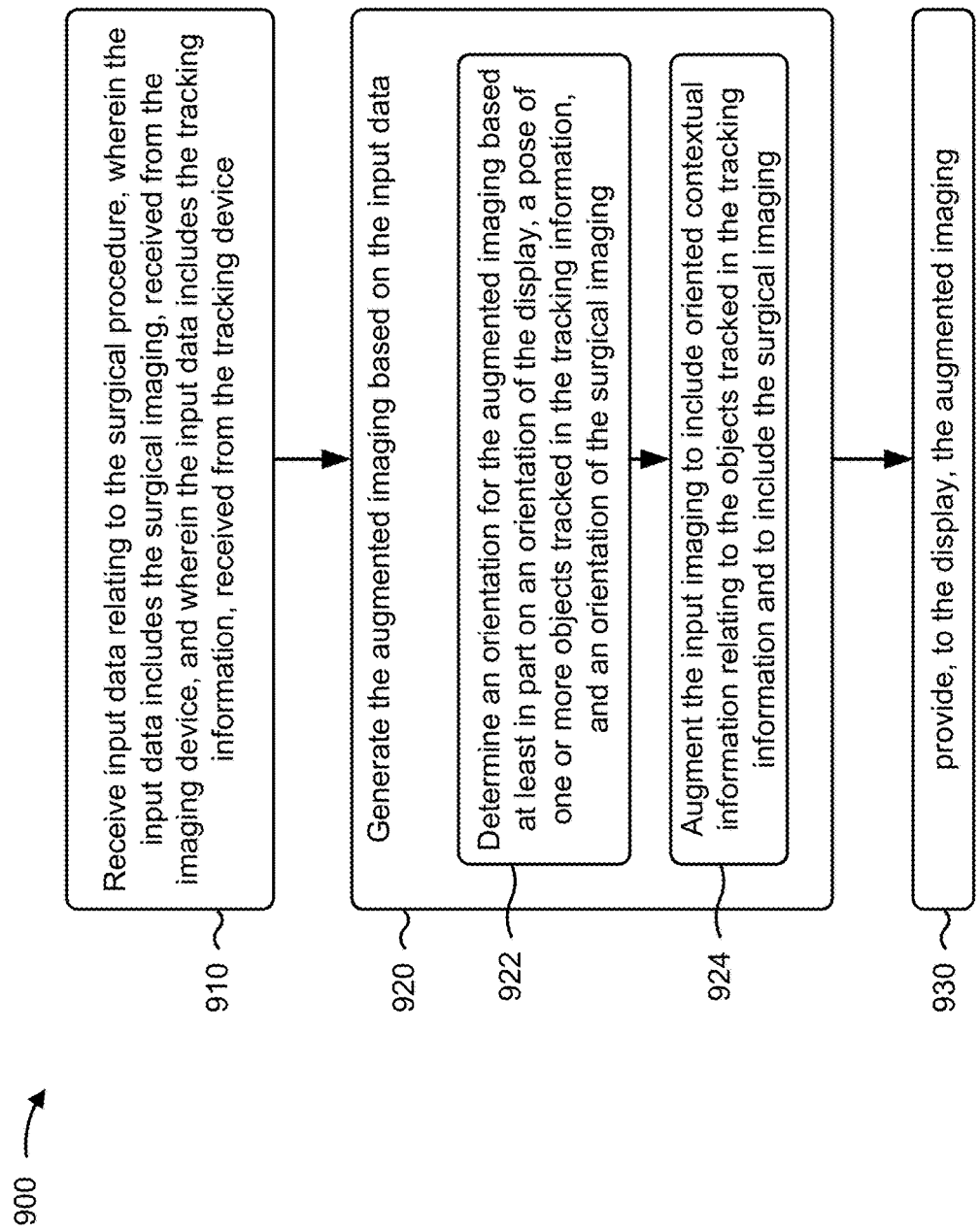
FIG. 9 is a flow chart of an example process for generating augmented imaging for a surgical procedure.

FIG. 9 is a flow chart of an example process 900 for generating augmented imaging for a surgical procedure. In some implementations, one or more process blocks of FIG. 9 may be performed by a visualization platform (e.g., visualization platform 750). In some implementations, one or more process blocks of FIG. 9 may be performed by another device or a group of devices separate from or including the visualization platform (e.g., visualization platform 750), such as a tracking device (e.g., tracking device 710), a display (e.g., display 730), a surgical robotics device (e.g., surgical robotics device 740), an imaging device (e.g., imaging device 760) and/or the like.

As shown in FIG. 9, process 900 may include receiving input data relating to the surgical procedure, wherein the input data includes the surgical imaging, received from the imaging device, and wherein the input data includes the tracking information, received from the tracking device (block 910). For example, the visualization platform (e.g., using a processor 820, a memory 830, a storage component 840, an input component 850, and a communication interface 870, and/or the like) may receive input data relating to the surgical procedure, as described above. In some implementations, the input data includes the surgical imaging, received from the imaging device. In some implementations, the input data includes the tracking information, received from the tracking device.

As further shown in FIG. 9, process 900 may include generating the augmented imaging based on the input data (block 920). For example, the visualization platform (e.g., using a processor 820, a memory 830, a storage component 840, an input component 850, and a communication interface 870, and/or the like) may generate the augmented imaging based on the input data, as described above.

As further shown in FIG. 9, process 900 and block 920 may include determining an orientation for the augmented imaging based at least in part on an orientation of the display, a pose of one or more objects tracked in the tracking information, and an orientation of the surgical imaging (block 922). For example, the visualization platform (e.g., using a processor 820, a memory 830, a storage component 840, an input component 850, and a communication interface 870, and/or the like) may determine an orientation for the augmented imaging based at least in part on an orientation of the display, a pose of one or more objects tracked in the tracking information, and an orientation of the surgical imaging, as described above.

As further shown in FIG. 9, process 900 and block 920 may include augmenting the input imaging to include oriented contextual information relating to the objects tracked in the tracking information and to include the surgical imaging (block 924). For example, the visualization platform (e.g., using a processor 820, a memory 830, a storage component 840, an input component 850, and a communication interface 870, and/or the like) may augment the input imaging to include oriented contextual information relating to the objects tracked in the tracking information and to include the surgical imaging, as described above.

As further shown in FIG. 9, process 900 may include providing, to the display, the augmented imaging (block 930). For example, the visualization platform (e.g., using a processor 820, a memory 830, a storage component 840, an output component 860, and a communication interface 870, and/or the like) may provide, to the display, the augmented imaging, as described above.

Process 900 may include additional implementations, such as any single implementation or any combination of implementations described below and/or in connection with one or more other processes described elsewhere herein.

In some implementations, the display may be a head-mountable display. In some implementations, the display may be an at least partially transparent display. In some implementations, the objects include a surgical implement of a surgical robotics device, and the tracking information includes information received from the surgical robotics device regarding the pose of the surgical implement. In some implementations, the objects include a handheld surgical implement, wherein the tracking information includes an image of a fiducial marker attached to the handheld surgical implement. In some implementations, the imaging device is a surgical scope.

In some implementations, the objects may include at least one of: a surgical implement, the display, the imaging device, the tracking device, or a person. In some implementations, the visualization platform may include one or more fiducial markers to enable motion tracking. In some implementations, the display may be a three-dimensional imaging display, and the augmented imaging may be three-dimensional imaging.

Although FIG. 9 shows example blocks of process 900, in some implementations, process 900 may include additional blocks, fewer blocks, different blocks, or differently arranged blocks than those depicted in FIG. 9. Additionally, or alternatively, two or more of the blocks of process 900 may be performed in parallel.

Figure 10:
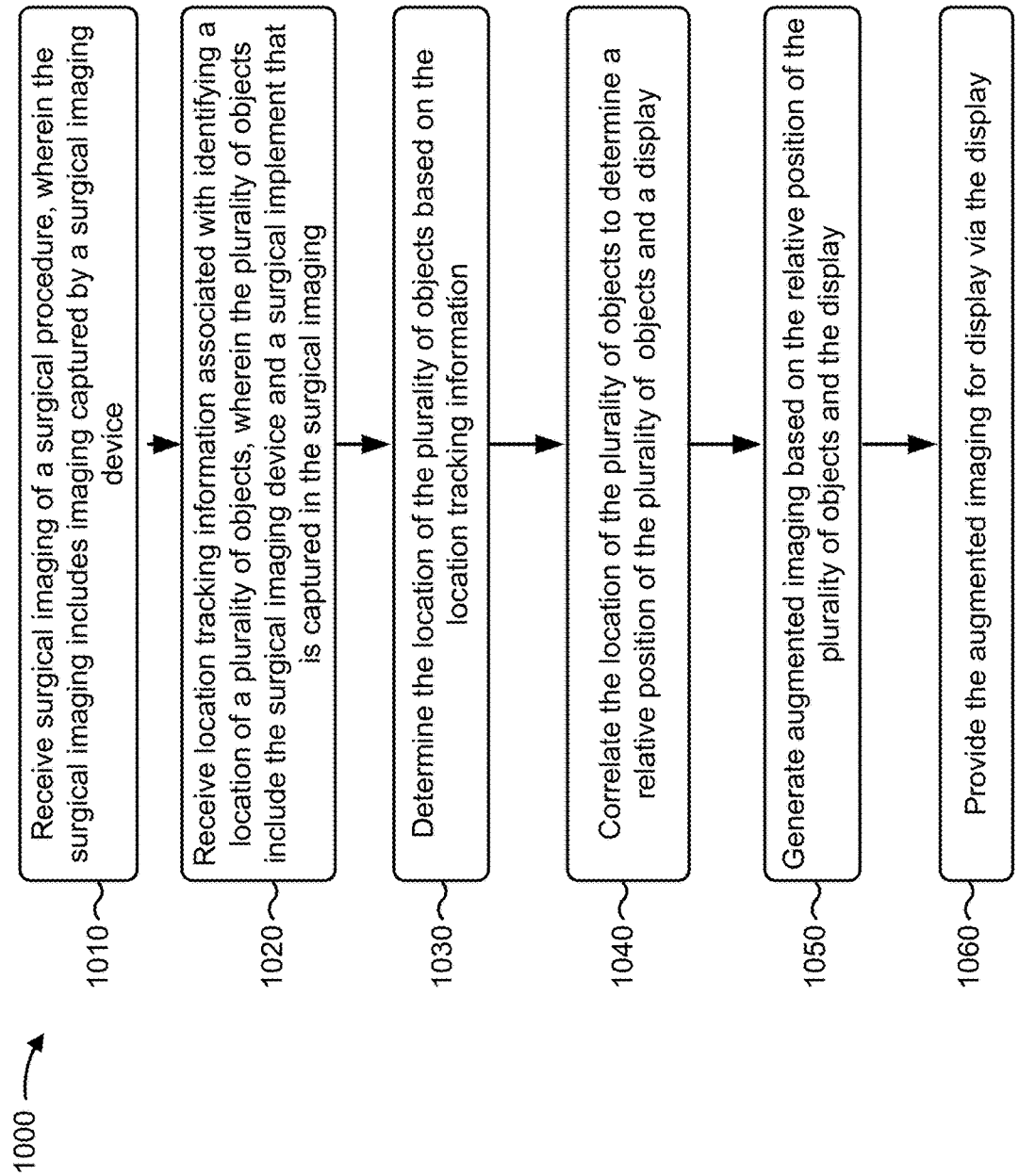
FIG. 10 is a flow chart of an example process for generating augmented imaging for a surgical procedure.

FIG. 10 is a flow chart of an example process 1000 for generating augmented imaging for a surgical procedure. In some implementations, one or more process blocks of FIG. 10 may be performed by a visualization platform (e.g., visualization platform 750). In some implementations, one or more process blocks of FIG. 10 may be performed by another device or a group of devices separate from or including the visualization platform (e.g., visualization platform 750), such as a tracking device (e.g., tracking device 710), a display (e.g., display 730), a surgical robotics device (e.g., surgical robotics device 740), an imaging device (e.g., imaging device 760) and/or the like.

As shown in FIG. 10, process 1000 may include receiving surgical imaging of a surgical procedure, wherein the surgical imaging includes imaging captured by a surgical imaging device (block 1010). For example, the visualization platform (e.g., using a processor 820, a memory 830, a storage component 840, an input component 850, and a communication interface 870, and/or the like) may receive surgical imaging of a surgical procedure, as described above. In some implementations, the surgical imaging includes imaging captured by a surgical imaging device.

As shown in FIG. 10, process 1000 may include receiving location tracking information associated with identifying a location of a plurality of objects, wherein the plurality of objects include the surgical imaging device and a surgical implement that is captured in the surgical imaging (block 1020). For example, the visualization platform (e.g., using a processor 820, a memory 830, a storage component 840, an input component 850, and a communication interface 870, and/or the like) may receive location tracking information associated with identifying a location of a plurality of objects, as described above. In some implementations, the plurality of objects include the surgical imaging device and a surgical implement that is captured in the surgical imaging.

As shown in FIG. 10, process 1000 may include determining the location of the plurality of objects based on the location tracking information (block 1030). For example, the visualization platform (e.g., using a processor 820, a memory 830, a storage component 840, an input component 850, and a communication interface 870, and/or the like) may determine the location of the plurality of objects based on the location tracking information, as described above.

As shown in FIG. 10, process 1000 may include correlating the location of the plurality of objects to determine a relative position of the plurality of objects and a display (block 1040). For example, the visualization platform (e.g., using a processor 820, a memory 830, a storage component 840, an input component 850, and a communication interface 870, and/or the like) may correlate the location of the plurality of objects to determine a relative position of the plurality of objects and a display, as described above.

As shown in FIG. 10, process 1000 may include generating augmented imaging based on the relative position of the plurality of objects and the display (block 1050). For example, the visualization platform (e.g., using a processor 820, a memory 830, a storage component 840, an input component 850, and a communication interface 870, and/or the like) may generate augmented imaging based on the relative position of the plurality of objects and the display, as described above.

As shown in FIG. 10, process 1000 may include provide the augmented imaging for display via the display (block 1060). For example, the visualization platform (e.g., using a processor 820, a memory 830, a storage component 840, an output component 860, and a communication interface 870, and/or the like) may provide the augmented imaging for display via the display, as described above.

Process 1000 may include additional implementations, such as any single implementation or any combination of implementations described below and/or in connection with one or more other processes described elsewhere herein.

In some implementations, the visualization platform may generate a field of view indicator identifying a field of view of the surgical imaging device. In some implementations, when generating the augmented imaging, the visualization platform may generate a visualization of one or more pre-operative medical images.

In some implementations, when generating the augmented imaging, the visualization platform may generate a visualization of an obscured portion of the surgical implement based on a model of the surgical implement, such that a portion of the model corresponding to the obscured portion of the surgical implement is visible in the augmented imaging. In some implementations, the visualization platform may transform an orientation of the surgical imaging based on the relative position of the one or more objects and the display.

Although FIG. 10 shows example blocks of process 900, in some implementations, process 1000 may include additional blocks, fewer blocks, different blocks, or differently arranged blocks than those depicted in FIG. 10. Additionally, or alternatively, two or more of the blocks of process 1000 may be performed in parallel.

Figure 11:
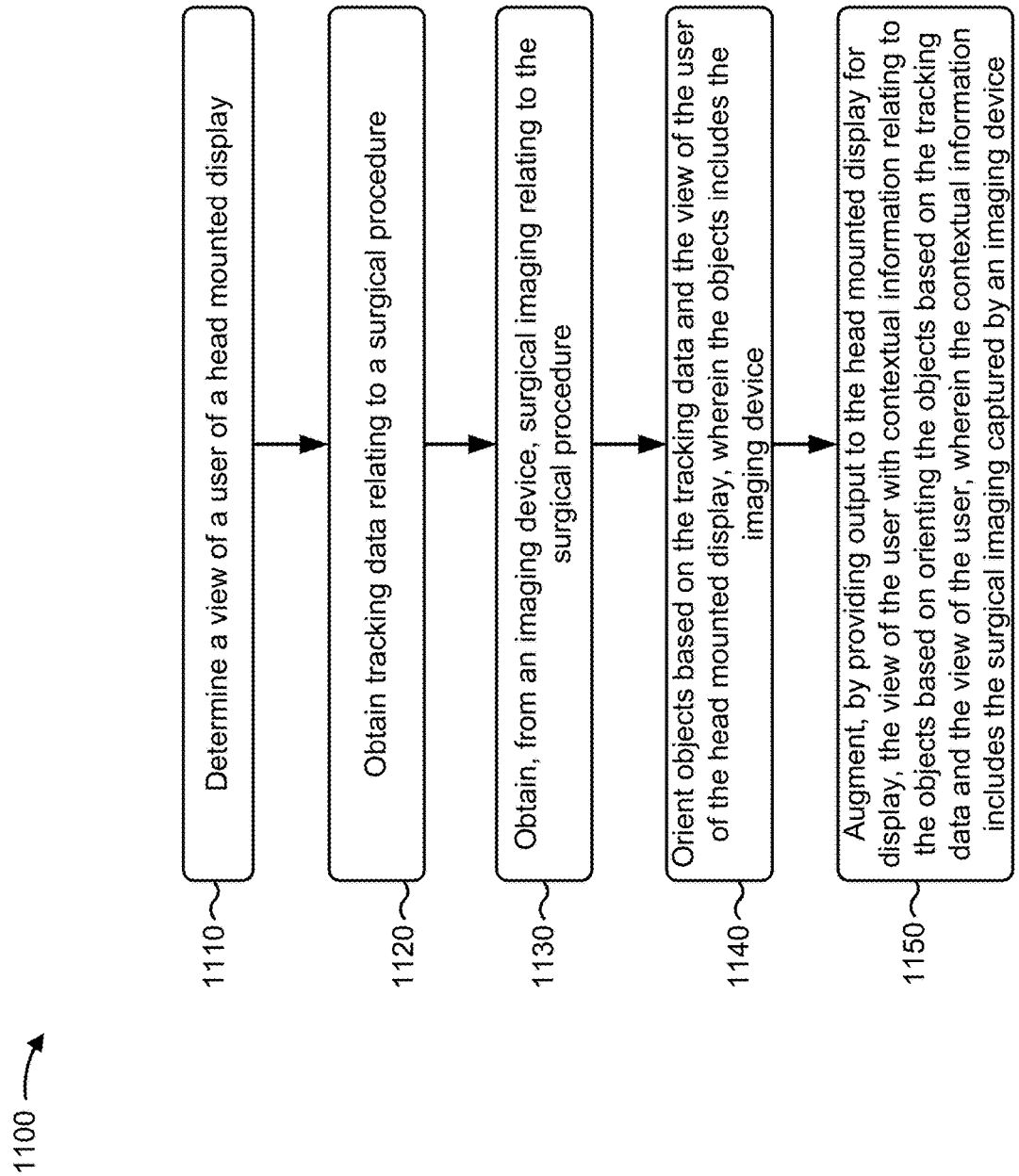
FIG. 11 is a flow chart of an example process for generating augmented imaging for a surgical procedure.

FIG. 11 is a flow chart of an example process 1100 for generating augmented imaging for a surgical procedure. In some implementations, one or more process blocks of FIG. 11 may be performed by a visualization platform (e.g., visualization platform 750). In some implementations, one or more process blocks of FIG. 11 may be performed by another device or a group of devices separate from or including the visualization platform (e.g., visualization platform 750), such as a tracking device (e.g., tracking device 710), a display (e.g., display 730), a surgical robotics device (e.g., surgical robotics device 740), an imaging device (e.g., imaging device 760) and/or the like.

As shown in FIG. 11, process 1100 may include determining a view of a user of a head mounted display (block 1110). For example, the visualization platform (e.g., using a processor 820, a memory 830, a storage component 840, an input component 850, and a communication interface 870, and/or the like) may determine a view of a user of a head mounted display, as described above.

As shown in FIG. 11, process 1100 may include obtaining tracking data relating to a surgical procedure (block 1120). For example, the visualization platform (e.g., using a processor 820, a memory 830, a storage component 840, an input component 850, and a communication interface 870, and/or the like) may obtain tracking data relating to a surgical procedure, as described above.

As shown in FIG. 11, process 1100 may include obtaining, from an imaging device, surgical imaging relating to the surgical procedure (block 1130). For example, the visualization platform (e.g., using a processor 820, a memory 830, a storage component 840, an input component 850, and a communication interface 870, and/or the like) may obtain, from an imaging device, surgical imaging relating to the surgical procedure, as described above.

As shown in FIG. 11, process 1100 may include orienting objects based on the tracking data and the view of the user of the head mounted display, wherein the objects include the imaging device (block 1140). For example, the visualization platform (e.g., using a processor 820, a memory 830, a storage component 840, an input component 850, and a communication interface 870, and/or the like) may orient objects based on the tracking data and the view of the user of the head mounted display, as described above. In some implementations, the objects include the imaging device.

As shown in FIG. 11, process 1100 may include augmenting, by providing output to the head mounted display for display, the view of the user with contextual information relating to the objects based on orienting the objects based on the tracking data and the view of the user, wherein the contextual information includes the surgical imaging captured by an imaging device (block 1150). For example, the visualization platform (e.g., using a processor 820, a memory 830, a storage component 840, an input component 850, and a communication interface 870, and/or the like) may augment, by providing output to the head mounted display for display, the view of the user with contextual information relating to the objects based on orienting the objects based on the tracking data and the view of the user, as described above. In some implementations, the contextual information includes the surgical imaging captured by an imaging device.

Process 1100 may include additional implementations, such as any single implementation or any combination of implementations described below and/or in connection with one or more other processes described elsewhere herein.

In some implementations, the contextual information includes a field-of-view indicator of the imaging device determined based on the tracking data and the view of the user.

In some implementations, the visualization platform may receive information identifying an implement of a surgical robotics device, determine a model of the implement of the surgical robotics device, and augment the view of the user to include the model of the implement of the surgical robotics device. In some implementations, the visualization platform may provide the input imaging at a fixed position in the view of the user, the input imaging via a virtualized display selectively in the view of the user, or the input imaging at a location in the view of the user at which the input imaging is being captured.

In some implementations, the visualization platform may detect a change to a direction of the view of the user, and may alter a position of one or more augmented elements in the view of the user based on detecting the change to the direction of the view of the user. In some implementations, the visualization platform may detect a change to a surgical implement attached to a surgical robotics device, may update a model of the surgical implement based on the change, and may update the output to the head mounted display based on updating the model of the surgical implement.

In some implementations, imaging may be at least one of: real-time video imaging from a fixed image capture device, real-time video imaging from an endoscope, pre-operation static imaging from a medical imaging device, or real-time static imaging from the medical imaging device.

Although FIG. 11 shows example blocks of process 1100, in some implementations, process 1100 may include additional blocks, fewer blocks, different blocks, or differently arranged blocks than those depicted in FIG. 11. Additionally, or alternatively, two or more of the blocks of process 1100 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A system, comprising:
    an imaging device configured to capture surgical imaging relating to a surgical procedure;
    a tracking device configured to capture tracking information relating to the surgical procedure;
    a display configured to provide augmented imaging relating to the surgical procedure; and
    a visualization platform configured to:
        receive input data relating to the surgical procedure,
            wherein the input data includes the surgical imaging and the tracking information,
                the surgical imaging being received from the imaging device, and
                the tracking information being received from the tracking device;
        generate the augmented imaging based on the input data,
            wherein the visualization platform, to generate the augmented imaging, is configured to:
                determine, based on the input data:
                    an orientation for the augmented imaging based at least in part on an orientation of the display,
                    a pose of a robotics implement, inside a patient, tracked in the tracking information, and
                    an orientation of the surgical imaging, and
                generate the augmented imaging to include oriented contextual information relating to the robotics implement and to include the surgical imaging; and
        provide, to the display, the augmented imaging.

2. The system of claim 1, wherein the display is a head-mountable display.

3. The system of claim 1, wherein the display is an at least partially transparent display.

4. The system of claim 1,
    wherein the tracking information includes information received from a surgical robotics device regarding a type of the robotics implement.

5. The system of claim 1,
    wherein the tracking information includes an image of a fiducial marker attached to a handheld surgical implement.

6. The system of claim 1, wherein the imaging device is a surgical scope.

7. The system of claim 1, wherein one or more objects tracked in the tracking information include at least one of:
    a surgical implement,
    the display,
    the imaging device,
    the tracking device, or
    a person.

8. The system of claim 1, further comprising:
    one or more fiducial markers to enable motion tracking.

9. The system of claim 1, wherein the display is a three-dimensional imaging display, and the augmented imaging is three-dimensional imaging.

10. A device, comprising:
    one or more memories; and
    one or more processors, communicatively coupled to the one or more memories, to:
        receive surgical imaging of a surgical procedure,
            wherein the surgical imaging includes imaging captured by a surgical imaging device;
        receive location tracking information associated with identifying a location of a plurality of objects,
            wherein the plurality of objects include the surgical imaging device and a robotics implement inside a patient;
        determine the location of the plurality of objects based on the location tracking information;
        correlate the location of the plurality of objects to determine a relative position of the plurality of objects and a display;
        generate augmented imaging based on a pose of the robotics implement inside the patient and the relative position of the plurality of objects and the display; and
        provide the augmented imaging for display via the display.

11. The device of claim 10, wherein the one or more processors, when generating the augmented imaging, are to:
    generate a field of view indicator identifying a field of view of the surgical imaging device.

12. The device of claim 10, wherein the one or more processors, when generating the augmented imaging, are to:
    generate a visualization of one or more pre-operative medical images.

13. The device of claim 10, wherein the one or more processors, when generating the augmented imaging, are to:
    generate a visualization of an obscured portion of the robotics implement based on a model of the robotics implement, such that a portion of the model corresponding to the obscured portion of the robotics implement is visible in the augmented imaging.

14. The device of claim 10, wherein the one or more processors, when generating the augmented imaging, are to:

transform an orientation of the surgical imaging based on the relative position of one or more objects, of the plurality of objects, and the display.

15. A method, comprising:
determining, by a device, a view of a user of a head mounted display;
obtaining, by the device, tracking data relating to a surgical procedure;
obtaining, by the device and from an imaging device, surgical imaging relating to the surgical procedure;
orienting, by the device, objects based on the tracking data and the view of the user of the head mounted display,
wherein the objects include the imaging device and a robotics implement; and
augmenting, by the device and by providing output to the head mounted display for display, the view of the user with contextual information relating to the objects based on orienting the objects based on the tracking data and the view of the user,
wherein the contextual information includes the surgical imaging captured by the imaging device and a pose of the robotics implement inside a patient.

16. The method of claim 15, wherein the contextual information includes a field-of-view indicator of the imaging device determined based on the tracking data, design parameters of the imaging device and the view of the user.

17. The method of claim 15, further comprising:
receiving information identifying the robotics implement;
determining a model of the robotics implement; and
wherein augmenting the view of the user comprises:
augmenting the view of the user to include the model of the robotics implement.

18. The method of claim 15, wherein augmenting the view of the user comprises at least one of:
providing input imaging at a fixed position in the view of the user,
providing the input imaging via a virtualized display selectively in the view of the user, or
providing the input imaging at a location in the view of the user at which the input imaging is being captured.

19. The method of claim 15, further comprising:
detecting a change to a direction of the view of the user; and
altering a position of one or more augmented elements in the view of the user based on detecting the change to the direction of the view of the user.

20. The method of claim 15, further comprising:
detecting a change to a surgical implement attached to a surgical robotics device;
updating a model of the surgical implement based on the change; and
updating the output to the head mounted display based on updating the model of the surgical implement.

* * * * *